Figure 1:
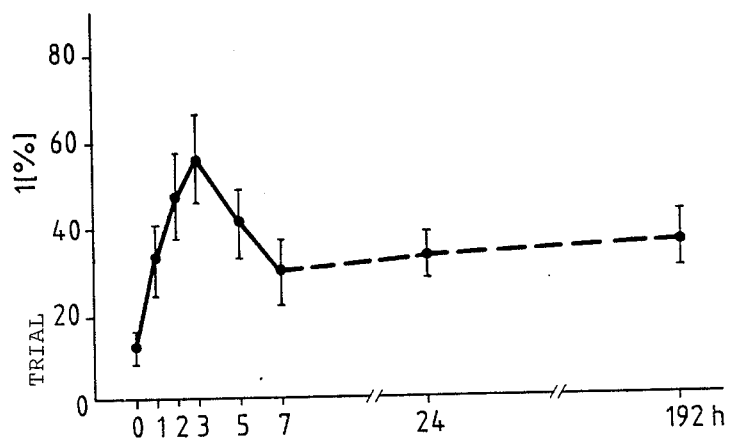
Figure 1:
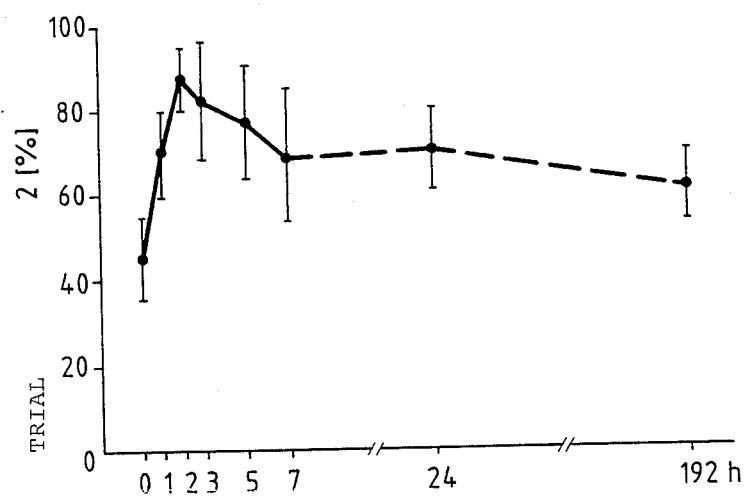

United States Patent [19]

Emrich

[11] Patent Number: 4,955,390

[45] Date of Patent: Sep. 11, 1990

[54] PROCESS FOR THE DETERMINATION OF THE PRESENCE OF A PSYCHEDELIC STATE

[76] Inventor: Hinderk M. Emrich, Theodolindenstrasse 6, D-8000 München 90, Fed. Rep. of Germany

[21] Appl. No.: 315,467

[22] Filed: Feb. 24, 1989

[30] Foreign Application Priority Data

Feb. 25, 1988 [DE] Fed. Rep. of Germany ....... 3805983

[51] Int. Cl.$^5$ ............................................. A61B 13/00
[52] U.S. Cl. .................................... 128/745; 128/898
[58] Field of Search .................... 128/25 A, 745, 897, 128/898; 434/236; 351/201, 203

Primary Examiner—Randall L. Green
Assistant Examiner—Randy Shay
Attorney, Agent, or Firm—Felfe & Lynch

[57] ABSTRACT

The present invention provides a process for the determination of the presence of a psychedelic state in a person, wherein the test subject is presented with a three-dimensional, stereoscopically inverted image of an object and there is determined whether said subject sees this image convexly or concavely within a predetermined period of time.

The present invention also provides an arrangement for the determination of the presence of a psychedelic state and especially of one due to the influence of a psychedelic drug, comprising a combination (a) of a device for the presenting of a three-dimensional image, (b) of at least one image which, in the device (a), depicts three-dimensionally an object in stereoscopically inverted representation and (c) at least one image which depicts the subject of image (b) in natural three-dimensional form.

3 Claims, 1 Drawing Sheet

PROCESS FOR THE DETERMINATION OF THE PRESENCE OF A PSYCHEDELIC STATE

The present invention is concerned with a process for the ascertainment of a psychedelic state.

It is known that a number of drugs are able to bring about an expansion of the consciousness, i.e. are psychedelic. This action is regarded as being one of the most important reasons for the misuse of these drugs. The detection of whether such a psychedelic state brought about by drugs is present could, however, hitherto only be carried out indirectly by chemical analysis for the presence of such drugs in the blood of the person being investigated or, in the case of some drugs, can practically not be carried out at all. However, the presence of the drugs does not permit safe conclusions of the actual presence of a psychedelic state. Whereas in the case of non-psychedelically active drugs, such as alcohol, methods have been developed for the ascertainment of the action of such drugs, for example in the scope of the determination of the capability of driving a motor vehicle, such a dependable method of determination for the presence of a psychedelic state is completely lacking. However, precisely because of the problems connected with the misuse of drugs, there is a need for such a dependable detection.

However, psychedelic drugs are also of great interest from a scientific point of view and also from this point of view there is a need for a dependable system for the detection of the presence of a psychedelic state brought about by the action of drugs.

It is an object of the present invention to provide a process for the determination of the presence of a psychedelic state and a device suitable for carrying out the process.

Thus, according to the present invention, there is provided a process for the determination of the presence of a psychedelic state in a person, especially of a psychedelic state due to the influence of psychedelic drugs, wherein the test subject is presented with a three-dimensional, pseudoscopic image of an object and there is determined whether said subject sees this image convexly or concavely within a predetermined period of time. In other words, there is ascertained whether a visually inverted image is observed or the actually shown pseudoscopic image.

The present invention is based on the fact that the image of an object, when it does not correspond to its actual known normal form of appearance but rather is stereoscopically inverted as in the case of a matrix for the production of a casting of this object, is, on the basis of experience, automatically corrected by the brain as the object normally appears and is so seen by the person as it corresponds to his own experience and not in the actually shown stereoscopically inverted form. Thus, typically, the hollow mask of a human face in the case of three-dimensional stereoscopic detection, i.e. in concave form, is seen inverted by the viewer without it being necessary for him to know and, therefore, appears convex. The present invention is based upon the surprising finding that in the case of the presence of a psychedelic state, such as occurs in the case of the administration of correspondingly effective drugs, this automatic visual inversion is disturbed and occurs either only chronologically delayed or not at all. Therefore, the present invention makes it possible to ascertain the presence of such a psychedelic state without any manipulations of the body itself having to be made.

The process according to the present invention is preferably carried out in such a manner that the person being examined is first shown a three-dimensional image of an object in the normal form and thereafter is shown the same object in a stereoscopically inverted form. Normally, this will take place in such a manner that the object to be shown, for example a part of the body or any other suitable object familiar to an average person (semantically relevant), is present in its usual convex form and thereafter the same object is shown expediently with the use of the same pictorial illustration in stereoscopically inverted and thus concave form. In order to determine whether the object is now seen in convex or concave form, the test subject is given a definite period of time, advantageously from 10 seconds to 2 minutes and preferably from 20 seconds to 1 minute. However, for certain purposes, shorter or longer test times can also be considered since the rapidity of the visual image inversion permits conclusions to be drawn with regard to the degree of the psychedelic state.

The present invention also provides an arrangement for the determination of the presence of a psychedelic state, comprising a combination (a) of a device for the presenting of a three-dimensional image, (b) of at least one image which depicts three-dimensionally in the device (a) an object in pseudoscopic representation and (c) of at least one image which depicts the subject of image (b) in natural, three-dimensional form.

The arrangement according to the present invention preferably contains additional means with which the test subject can signal within a predetermined period of time whether he sees the object depicted in the image in concave or convex form. Such a means can consist of a recording device to be operated by a press button which is arranged to reproduce and/or store the signal "concave" or "convex" but can also be a sheet of paper on which the appearance "concave" or "convex" is marked, for example by a cross.

The device (a) for displaying a three-dimensional image in the scope of the arrangement according to the present invention preferably contains a stereoscope, projector or monitor which reproduces or projects images providing the stereoscopic illustration of an object, as well as observation devices similar to spectacles. Such devices for the showing of three-dimensional images are known to the expert and do not here require any detailed explanation. Typical examples thereof include optical devices such as are known, for example, under the designation View-Master in which diapositives or other representations of the object to be shown are viewed by both eyes through ocular lenses and provide a three-dimensional impression of the object. Other examples include diaprojectors, stereotelevision pictures with two monitors which are viewed through appropriate spectacles or projectors, monitors or television pictures with overlapping projection of different coloured, different polarised pictures of the object to be shown or three-dimensional pictures according to the Polaroid 3D Vectograf® system which are viewed by the observer through an appropriate spectacle-like device with appropriate glasses differently polarised or coloured for the two eyes or prismatic glasses with differing light passage.

The following Example is given for the purpose of illustrating the present invention:

Healthy test subjects were placed in a psychedelic state by means of cannabis and the presence thereof tested as follows:

6 different stereoscopic diapositives (bushes, flowers, buildings shown inverted, teddy bear masks; inverted garden stools; inverted human faces) are shown by means of a device which contains two diapositive projectors with the use of linear polarised light orientated via a cross and spectacles with corresponding polarisation filters. By the exchange of the filter from the right eye to the left and vice versa, there is produced a binocular depth inversion of the three-dimensional image. During the projection, the test subject describes his visual impression according to the following procedure:

Experiment 1 detects the values for 4 diapositives of semantically relevant objects (an inverted house; a teddy mask, a garden stool turned upside down, an inverted human face). For each diapositive, three features are given which characterise the binocular impression of depth of special parts of the illustrated object (for example nose, eyes, cheeks, roof etc.). When all three characteristics are not appreciated as being inverted within 30 seconds, there is given the maximum point value of 2. A similar procedure is employed in the case of experiment 2 (diapositives of bushes, flowers). Thus, in experiment 1 there can be achieved a maximum of 8 points (=100%) and in experiment 2 a maximum of 4 points (=100%). The results of a control group of 20 test subjects without the administration of cannabis is given in the following Table.

7 test subjects who, in the scope of a controlled self experiment, had taken 222 to 373 mg. of cannabis resin (2.97 to 4.05 mg./kg. body weight) were investigated in the same way within a period of time of from 0 to 122 hours after taking the drug. The results are shown in FIG. 1 of the accompanying drawings. In experiment 1, the average point value which reflects the reduction of the binocular depth inversion of semantically relevant objects (house, human face; teddy mask; garden stool) increases from $12.5 \pm 11.4\%$ to a maximum average value of $56.6 \pm 10.0\%$ within 3 hours of taking the cannabis and decreases within 8 days (192 hours) to values of $36.5 \pm 15.2\%$. In the case of experiment 2, which reflects the reduction of the binocular depth inversion of semantically less relevant objects (flowers; bushes), it begins with a higher average value of $54.4 \pm 25.3\%$ of the maximum value and achieves, 2 hours after taking the cannabis, a maximum of $87.5 \pm 19.1\%$. After 8 days (192 hours), the lowering of the evaluation is less marked and amounts to $61.0 \pm 18.4\%$.

The results of these experiments show that, with the process according to the present invention, the psychedelic state brought about by taking drugs can still be detected 8 days after taking the drug.

TABLE

| experiment No. | Control group $\bar{x}$ | SD |
|---|---|---|
| 1 | 10.8% | 13.6% |
| 2 | 51.3% | 23.3% |

It will be understood that the specification and examples are illustrative but not limitative of the present invention and that other embodiments within the spirit and scope of the invention will suggest themselves to those skilled in the art.

I claim:

1. A process for the determination of the presence of a psychedelic state in a test subject comprising:
   presenting the test subject with a three-dimensional, stereoscopically inverted image of an object, and
   determining whether said test subject sees this image convexly or concavely within a predetermined period of time by means of a signal from the test subject.

2. The process of claim 1 further comprising presenting the image of the object first in the natural three-dimensional representation and then second in a stereoscopically inverted representation.

3. The process of claim 1 further comprising determining the convexity or concavity of the image by the signal from the test subject wherein the signal is given in a time of from 10 sec. to 2 min. from presentation of the stereoscopically inverted image.

* * * * *